US005591442A

United States Patent [19]

Diehl et al.

[11] Patent Number: 5,591,442

[45] Date of Patent: Jan. 7, 1997

[54] SKIN ANTISEPTIC AND HAND DISINFECTANT

[75] Inventors: Karl H. Diehl, Norderstedt; Heinz Eggensperger, Hamburg; Peter Goroncy-Bermes, Ahrensburg; Peter Oltmanns; Susanne Toefke, both of Hamburg, all of Germany

[73] Assignee: Reckitt & Colman Inc., Montvale, N.J.

[21] Appl. No.: 513,420

[22] Filed: Aug. 15, 1995

Related U.S. Application Data

[63] Continuation of Ser. No. 979,715, Nov. 20, 1992, abandoned.

[30] Foreign Application Priority Data

Dec. 9, 1991 [DE] Germany .......................... 41 40 473.4

[51] Int. Cl.$^6$ ................................ A61K 6/00; A61K 7/00

[52] U.S. Cl. .......................... 424/401; 424/70.1; 424/61; 422/61

[58] Field of Search .................................. 424/401, 70.1, 424/61

[56] References Cited

U.S. PATENT DOCUMENTS

| | | | |
|---|---|---|---|
| 3,959,185 | 5/1976 | Barillo | 424/70 |
| 4,416,808 | 11/1983 | Blaschke et al. | 252/547 |
| 4,781,916 | 11/1988 | Papaphilippou | 424/61 |
| 4,820,717 | 4/1989 | Mosse et al. | 514/317 |
| 4,954,338 | 9/1990 | Mattox | 424/78 |
| 5,117,032 | 5/1992 | Fabry | 558/34 |

FOREIGN PATENT DOCUMENTS

| | | |
|---|---|---|
| 0649206 | 9/1934 | Germany . |
| 649206 | 8/1937 | Germany . |

*Primary Examiner*—Thurman K. Page
*Assistant Examiner*—William E. Benston, Jr.
*Attorney, Agent, or Firm*—Frederick H. Rabin; John R. Everett

[57] ABSTRACT

A skin antiseptic and hand disinfectant composition is disclosed. The composition comprises a glycerol monoalkyl ether is a glycerol 1-$C_5$–$C_{12}$ alkyl ether and an aliphatic $C_1$–$C_6$ alkyl alcohol.

10 Claims, 2 Drawing Sheets

SKIN ANTISEPTIC AND HAND DISINFECTANT

This application is a continuation, of application No. 07/979715, filed 20 Nov. 1992, now abandoned.

FIELD OF THE INVENTION

This invention relates to skin antiseptic and hand disinfectant compositions.

BACKGROUND OF THE INVENTION

Parts of the skin and mucous membranes have long been treated antiseptically prior to surgical intervention, injections or punctures and prior to examinations of body cavities accessible from the outside. Moreover, it is necessary also for those persons who carry out the above treatments and examinations to disinfect their hands before the treatment or examination commences.

For such purposes known compositions with antiseptic action are highly volatile alcohols. However, high alcohol concentrations must be present for effectiveness within a very short contact time (within seconds to a few minutes). The alcohol content is generally more than 50, mostly about 60 to 80% by wt. The alcohols are frequently aliphatic alcohols such as ethanol, 1-propanol and 2-propanol.

In addition to alcohols, hand disinfectants frequently contain other substances such as long-acting active cationic compounds with an antimicrobial action, and skin care components in order to prevent severe drying of the skin. In the case of skin antiseptics containing lipid restorers, the alcohol content must often be higher than in preparations without lipid restoring agents, since said compounds often impair the antiseptic effectiveness of the alcohols or other microbial active ingredients present.

In spite of the lipid restoring skin care components, and given the necessarily frequent use of said preparations, irritation of the skin treated therewith occurs to an increased extent at colder times of the year.

Apart from alcoholic skin antiseptics and hand disinfectants, antimicrobial and disinfectant aqueous emulsions are also known which contain a glycerol monoalkyl ether., e.g. 3-alkoxypropan-1,2-diol (known for example from U.S. Pat. No. DE 649 206). The antimicrobial effectiveness of glycerol ethers (e.g. also known from JP 76-76424) when used alone has proved to be relatively poor in practice, however, so that their use as an active ingredient in skin antiseptics containing substantial quantities of water is completely inadequate without other additives also having an antimicrobial action.

It is an object of the invention to provide a particularly skin-compatible skin antiseptic and hand disinfectant that 1) has a lasting lipid-restoring effect and hence cares for the skin; 2) and yet is a quick-acting antiseptic which capacity and ease of application is not impaired by skin care components and 3) gives a pleasant feel to the skin.

SUMMARY OF THE INVENTION

Figure 1:
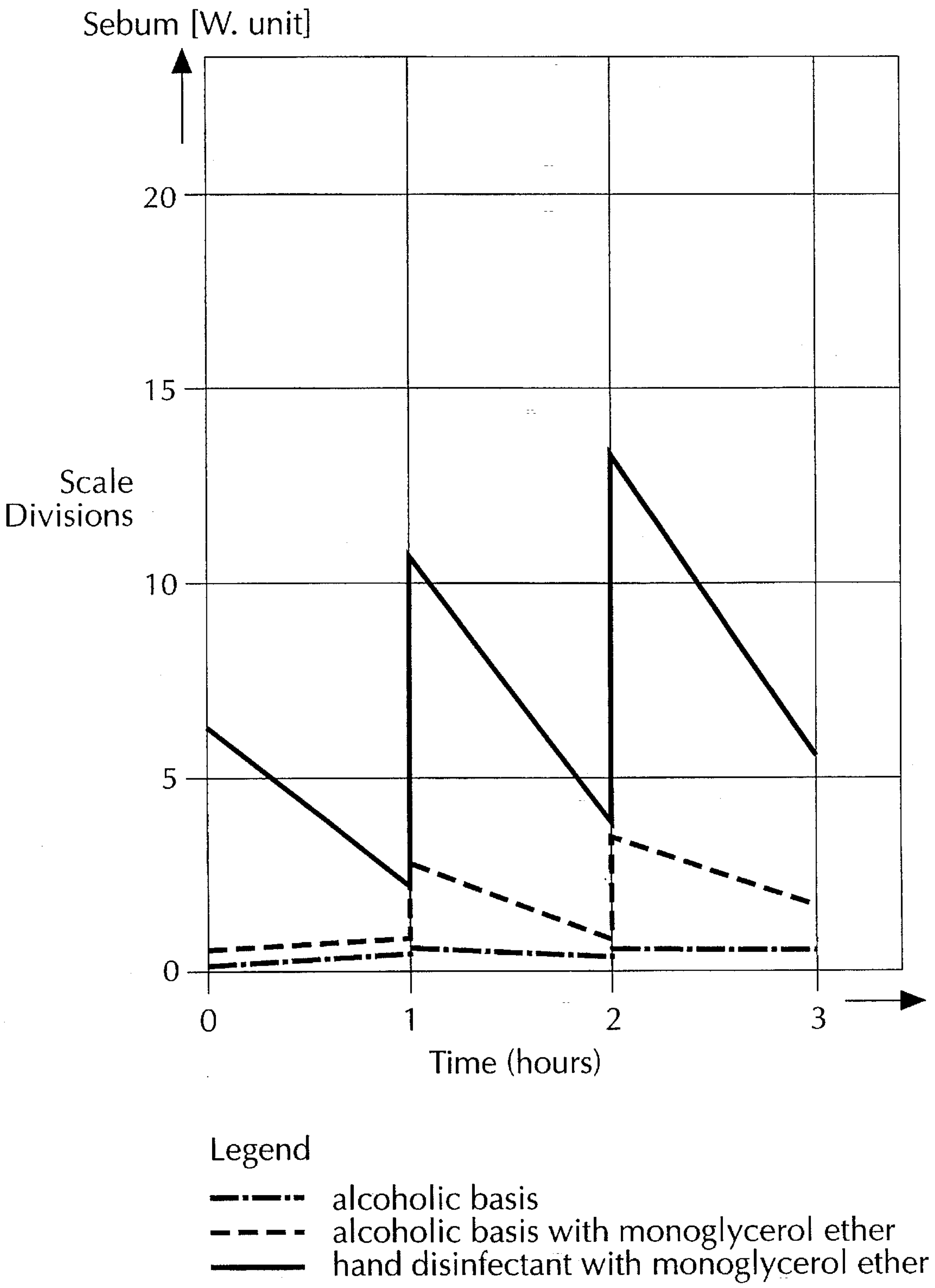
FIG. 1 show the slight increase in oil concentration on skin treated with compositions of the invention.

This object is achieved by an aqueous composition comprising an alkyl alcohol component and at least one glycerol monoalkyl ether. It was found that this composition exhibits an outstanding antimicrobial effect and at the same time restores the lipid content of the skin.

This is particularly surprising because the glycerol monoalkyl ethers themselves exhibit insufficient antimicrobial action and their lipid restoring properties are hitherto unknown.

The antimicrobial effectiveness of the composition according to the invention is greater than that of the individual alkyl alcohol components or glycerol monoalkyl ether alone. There is, therefore, a genuine synergism.

In view of the synergistic effect of the alkyl alcohol component and the glycerol monoalkyl ether, it is possible to reduce the alkyl alcohol content of the composition compared with that of the well known compositions used as skin antiseptics and hand disinfectants.

The combination of alkyl alcohols in low concentrations with a glycerol monoalkyl ether offers economic advantages by reducing the alcohol content and but also the possibility of improving the compatibility of skin antiseptics and hand disinfectants to skin. The risk of skin irritation is reduced considerably, particularly with frequent use, because of the reduced drying and better lipid-restoring effect of the composition.

As a result of the addition according to the invention of glycerol monoalkyl ether in small quantities to an alkyl alcohol component, it has now proved possible to achieve a sufficiently high efficiency and rapid onset of action and a markedly good lipid-restoring effect.

The glycerol monoalkyl ethers are in particular glycerol 1-($C_5$–$C_{12}$ alkyl) ethers. These include, amongst others, glycerol 1-(2-ethylhexyl) ether, glycerol 1-heptyl ether, glycerol 1-octyl ether, glycerol 1-decyl ether and glycerol 1-dodecyl ether. A preferred compound is glycerol 1-(2-ethylhexyl) ether. These compounds are readily obtainable. Their preparation is described in the literature, e.g. in JP 80-19253, JP 58-134049, U.S. Pat. No. DE 33 43 530 and E. Baer, H. O. L. Fischer in J. Biol. Chem. 140 397 (1941).

The composition according to the invention contains as alkyl alcohol component at least one aliphatic C1–$C_6$ alkyl alcohol. In particular, aliphatic alkyl alcohols such as ethanol, 1-propanol, 2-propanol or a mixture of two or more of said alcohols are suitable for this purpose.

Compositions according to the invention generally contain 15 to 85% by wt., in particular 20 to 50% by wt., preferably 25 to 40% by wt. and more preferably 30 to 35% by wt. alkyl alcohol component, 0.1 to 5% by wt., preferably 0.5 to 2.5% by wt. and more preferably 0.5 to 1.5% by wt. glycerol monoalkyl ether and water. In particular preference, the composition contains 35% by wt. alkyl alcohol component, 1% by wt. glycerol monoalkyl ether and water.

Moreover, the composition of the invention may contain one or several other compounds with antiseptic properties action, dye and/or perfume and other customary additives and auxiliaries such as surfactants. In contrast to the additives such as skin care additives optionally present in well known skin antiseptics and hand disinfectants, other additives present in the composition according to the invention do not impair the antiseptic action. As a result, the disadvantage of having to increase the alkyl alcohol concentration in the presence of such additives such as skin care components, for example, is also avoided.

The following examples 1 to 6 show possible formulations for compositions according to the invention:

| | |
|---|---|
| Example 1 | |
| Ethanol | 85 % |
| o-phenylphenol | 0.1 % |
| Glycerol 1-(2-ethylhexyl) ether | 1.5 % |
| Demineralized water | q.s. 100 % |
| Dye | |
| Perfume | |
| Example 2 | |
| 1-Propanol | 50 % |
| 2-Propanol | 20 % |
| Glycerol 1-(2-ethylhexyl) ether | 1 % |
| Demineralized water | q.s. 100 % |
| Dye | |
| Perfume | |
| Example 3 | |
| 2-Propanol | 70 % |
| Ethanol | 10 % |
| Glycerol 1-heptyl ether | 1.3 % |
| Demineralized water | q.s. 100 % |
| Dye | |
| Perfume | |
| Example 4 | |
| Ethanol | 45 % |
| Benzethonium chloride | 0.6 % |
| Glycerol 1-decyl ether | 0.5 % |
| Demineralized water | q.s. 100 % |
| Dye | |
| Perfume | |
| Example 5 | |
| 2-Propanol | 35 % |
| Lactic acid | 0.3 % |
| Glycerol 1-octyl ether | 0.8 % |
| Demineralized water | q.s. 100 % |
| Dye | |
| Perfume | |
| Example 6 | |
| 1-Propanol | 55 % |
| Ethanol | 15 % |
| Glycerol 1-(2-ethylhexyl) ether | 1.2 % |
| Demineralized water | q.s. 100 % |
| Dye | |
| Perfume | |

As has already been mentioned, alkyl alcohols are very effective against microorganisms, the action commencing within a relatively short time (a few minutes), but high concentrations must be chosen in order to achieve very short contact times (1 minute or less).

In a quantitative suspension test, the relationship was determined between the reaction time and the alcohol concentration with and without glycerol monoalkyl ether. As the results in Table 1 show, a reaction time of 120 seconds was required for a reduction in the bacterial count of Pseudomonas aeruginosa by more than 5 log steps with an alcohol concentration of 35% by wt., or at least a concentration of 40% ethanol was required to halve this reaction time to 60 seconds or less. In contrast, when a composition according to the invention is used, e.g. the addition of a glycerol monoalkyl ether in small quantities (1% by wt.) to 35% ethanol, a reaction time of only 60 seconds is sufficient to obtain the same reduction in the bacterial count. With the same alcohol concentration, therefore, the contact time could be reduced to one half or, looked at from the other way round, the ethanol content could be reduced by 5% by wt. (a reduction of 12.5%) with the same contact time.

TABLE I

Reduction in Bacterial Count of *S. aureus* and *P. aeruginosa* in the Quantitative Suspension Test

| Ethanol concentration in wt % | Exposure time in seconds 15 | 30 | 60 | 120 |
|---|---|---|---|---|
| *P aeruginosa* | | | | |
| 20% | 0 | 0 | 0 | 0 |
| 30% | 0 | 0 | 0 | 0 |
| 35% | 1.05 | 1.60 | 2.55 | ≧5.48 |
| 40% | ≧5.49 | ≧5.43 | ≧5.40 | ≧5.48 |
| 35% ethanol + 1% glycerol ether | | | ≧5.38 | |
| *S. aureus* | | | | |
| 35% | 0 | 0 | 0 | 1.16 |
| 40% | 0 | 1.11 | 2.04 | 5.09 |
| 35% ethanol + 1% glycerol ether | | | ≧5.44 | |

Even when 40% ethanol was used, a contact time of 120 seconds was required to reduce the bacterial count of Staphylococcus aureus by >5 log steps. On the other hand, the same reduction in the bacterial count could be achieved in 60 seconds with 35% ethanol in combination with 1% glycerol ether. In this case, therefore, both a reduction in the exposure time and a reduction in the alcohol concentration could be achieved.

The results of the above quantitative suspension tests was confirmed by tests on the skin of the lower arms of voluntary subjects. Table II shows the reduction factors that were obtained with 70% isopropanol (reference solution according to the DGHM* (German Society for Hygiene and Microbiology) code of practice for testing and evaluating skin disinfectants, situation on 1.1.91, Zbl. Hyg. 192 (1991), page 99–103) or 35% ethanol, and with a combination of 35% ethanol and 1% glycerol monoalkyl ether after a contact time of 30, 60 and 120 seconds. The results show that a combination of ethanol and glycerol ethylhexyl ether produces an effect which, on the one hand, goes beyond the extent to be expected and, on the other hand, is comparable with the effect of 70% isopropanol in spite of an alcohol content that has been reduced by one half. Since glycerol ether alone has antimicrobial action only to a minor extent, a synergistic effect must be assumed.

TABLE II

Reduction in Bacterial Count of *Micrococcus luteus* on Skin Williamson and Kligman Test

| | Reduction factor |
|---|---|
| Reaction time: 30 s | |
| 70% Isopropanol | 2.11 |
| 35% Ethanol | 0.37 |
| 35% Ethanol + 1% glycerol ethylhexyl ether | 1.62 |
| Reaction time: 60 s | |
| 70% Isopropanol | 2.30 |
| 35% Ethanol | 0.61 |
| 35% Ethanol + 1% glycerol ethylhexyl ether | 1.71 |
| Reaction time: 120 s | |
| 70% Isopropanol | 2.37 |
| 35% Ethanol | 0.65 |
| 35% Ethanol + 1% glycerol ethylhexyl ether | 1.79 |

Without the addition of alcohol, glycerol monoalkyl ethers as pure substances are sparingly soluble in water.

Aqueous suspensions of the ethers exhibit an insufficient microbial action. The above compositions according to Tables I and II were tested with the active ingredients ethanol and isopropanol individually and the combination ethanol and glycerol ether in aqueous solution. The test organisms used to test the microbicidal effect were *Staphylococcus aureus, Pseudomonas aeruginosa* and *Micrococcus luteus*. The bactericidal effect was determined in the quantitative suspension test according to the code of practice of the German Society for Hygiene and Microbiology (DGHM) and in the Williamson and Kligmann skin test.

A particular advantage of using glycerol ether arises from the fact that it exhibits outstanding lipid-restoring properties particularly in the low concentrations in which it contributes to the increase in the antimicrobial effectiveness. This is wholly in line with modern formulations in which, for reasons of better compatibility, as few as possible different ingredients should be used.

It can be shown in skin measurements that when used through the day the glycerol ether brings about a slight increase in the concentration of the lipid content on the skin, without this making itself noticeable in a negative way as a greasy film (see FIG. 1).

A sebumeter SM 810 PC from Courage and Khazaka, Cologne, was used as measuring apparatus. Every hour, 3 mL of hand disinfectant were rubbed for 90 seconds into the hands which had not been treated beforehand. After 3 hours, the test was halted. The measurements were carried out directly before and after each application, the back of each hand being measured twice and the palm of each hand being measured once (skin lipid measurements).

In order to demonstrate the superior lipid-restoring property of the glycerol ether-containing compositions according to the invention in comparison with well known hand disinfectants, measurements of the skin oil content were carried out with the sebumeter. The measuring conditions and the apparatus were the same as above.

The following formulations were tested on a comparative basis:

Formulation A

60% ethanol
20% i-propanol
q.s. 100% water

Formulation B

60% ethanol
20% i-propanol
1% glycerol 1-(2-ethylhexyl) ether
q.s. 100% water

Formulation C

60% ethanol
20% i-propanol
1% myristyl alcohol
q.s. 100% water

Formulation D

Figure 2:
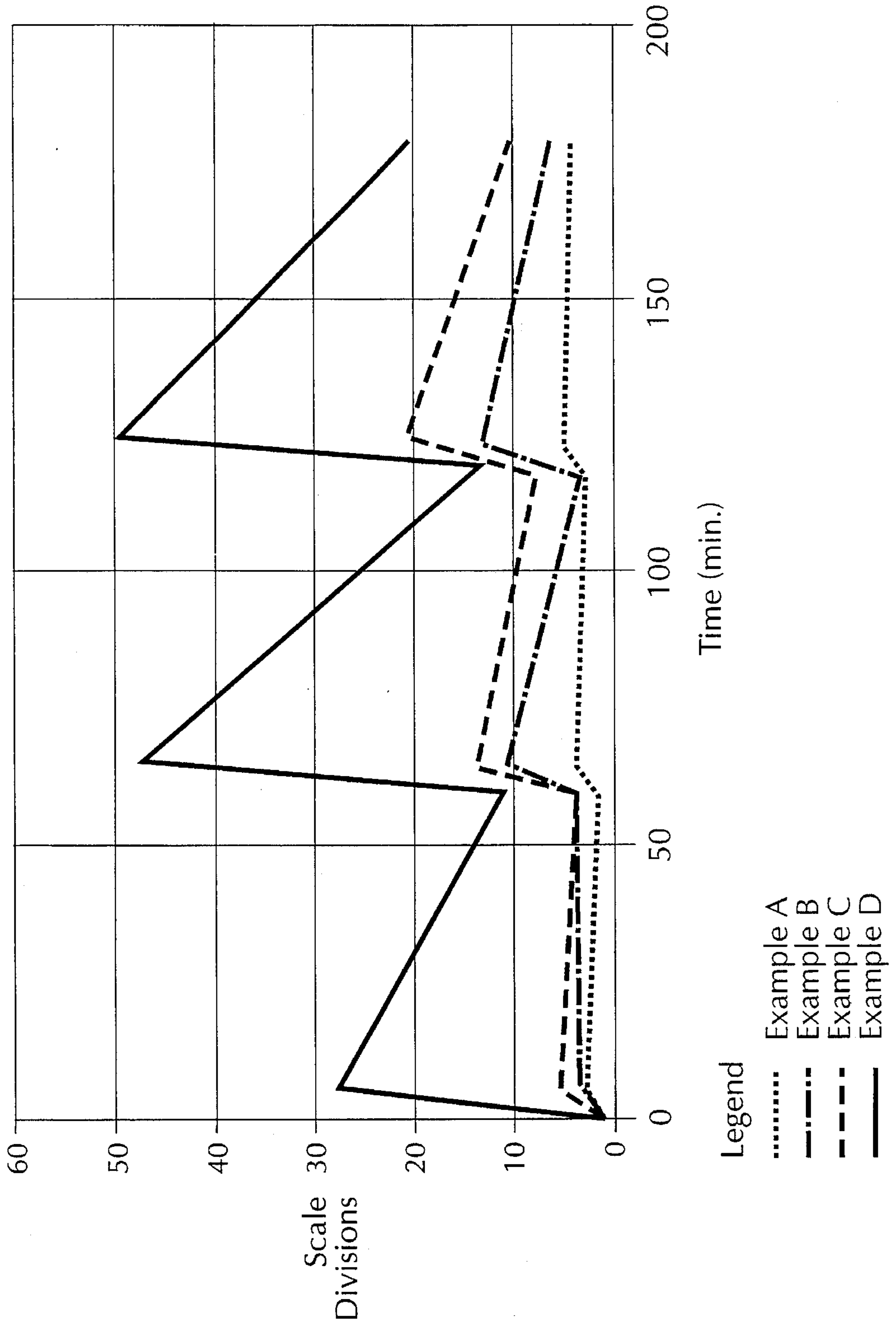
FIG. 2 illustrates the skin lipid restoring properties of monoalkyl glycerol ethers.

60% ethanol
20% i-propanol
1% myristyl alcohol
1% glycerol 1-(2-ethylhexyl) ether
q.s. 100% water The graphical plot of the sebumeter values obtained (see FIG. 2) illustrates the superior lipid-restoring effect brought about by the glycerol ether. In order to obtain a better comparison with the hand disinfectants known hitherto, a total alcohol content of 80% was chosen in all the formulations, which is customary in commercial preparations.

After the application of formulation B, there remains a higher skin lipid content after each application compared with the application of formulation A, the difference between the formulations being that formulation A contains no glycerol ether.

This effect becomes particularly pronounced in a comparison of formulations C and D. With formulation D, markedly higher skin lipid contents are achieved than with formulation C which already contains a well known lipid-restoring component (myristyl alcohol). The higher skin lipid content, which is obtained after application of formulation D, falls markedly within an hour of application but there remains a higher lipid content than after application of formulation C, particularly after repeated application.

The increased lipid-restoring property of the glycerol ethers in the compositions according to the invention is subjectively discernable by a pleasant feel to the skin that remains after application, which can be described with the adjectives velvety, soft, smooth, non-greasy and non-sticky.

The compositions according to the invention can be prepared by mixing the individual components together successively, if necessary with heating. No particular order need be adhered to during this process.

Seen as a whole, therefore, the compositions according to the invention are especially suitable as skin antiseptics and hand disinfectants.

The invention has been described in detail with particular reference to preferred embodiments thereof, but it will be understood that variations and modifications can be effected within the spirit and scope of the invention.

We claim:

1. A method for cleaning and disinfecting the skin which comprises applying to the skin an aqueous antiseptic and disinfectant composition comprising from 15 to 85% by weight of an aliphatic $C_1$–$C_6$ alkyl alcohol and from 0.1 to 5% by weight of a glycerol 1-($C_5$–$C_{12}$ alkyl) ether.

2. A skin antiseptic and hand disinfectant composition comprising a glycerol 1-($C_5$–$C_{12}$ alkyl) ether and an aliphatic $C_1$–$C_6$ alkyl alcohol.

3. A composition according to claim 2 wherein the glycerol ether is selected from the group consisting of glycerol 1-(2-ethylhexyl) ether, glycerol 1-heptyl ether, glycerol 1-octyl ether, glycerol 1-decyl ether and glycerol 1-dodecyl ether.

4. A composition according to claim 2 wherein the alkyl alcohol component contains ethanol, 1-propanol, 2-propanol or a mixture of two or more of said alcohols.

5. A composition according to claim 2 containing 15 to 85% by wt. alkyl alcohol and 0.1 to 5% by wt glycerol monoalkyl ether.

6. A composition according to claim 2 containing 20 to 50% by wt. of alkyl alcohol and 0.5–2.5% by wt. glycerol monoalkyl ether.

7. A composition according to claim 2 containing 25–40% by wt. alkyl alcohol and 0.5–1.5% by wt. glycerol monoalkyl ether.

8. A composition according to claim 2 containing 30–35% by wt. alkyl alcohol and 1% by wt. glycerol monoalkyl ether.

9. A composition according to claim 2 containing 35% by wt. alkyl alcohol and 1% by wt. glycerol monoalkyl ether.

10. The composition of claim 3 wherein the ether is 1-(2-ethylhexyl)glycerin ether.

* * * * *